(12) United States Patent
Sanandajifar

(10) Patent No.: US 10,726,990 B2
(45) Date of Patent: Jul. 28, 2020

(54) HIGH SPEED DATA TRANSFORMER FOR PATIENT ISOLATION BARRIER

(71) Applicant: Karl Storz Imaging, Inc., Goleta, CA (US)

(72) Inventor: Joseph Sanandajifar, Goleta, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 302 days.

(21) Appl. No.: 15/718,878

(22) Filed: Sep. 28, 2017

(65) Prior Publication Data

US 2019/0096574 A1 Mar. 28, 2019

(51) Int. Cl.
*H01F 17/04* (2006.01)
*H01F 38/14* (2006.01)
(Continued)

(52) U.S. Cl.
CPC ............. *H01F 38/14* (2013.01); *H01F 19/04* (2013.01); *H01F 27/027* (2013.01); *H01F 27/06* (2013.01); *H01F 27/24* (2013.01); *H01F 27/266* (2013.01); *H01F 27/2823* (2013.01); *H01F 27/2828* (2013.01); *H02J 50/80* (2016.02); *A61B 1/00011* (2013.01); *A61B 1/00018* (2013.01); *A61N 1/08* (2013.01); *H01F 2019/085* (2013.01); *H01F 2027/065* (2013.01)

(58) Field of Classification Search
USPC .......... 336/221, 222, 212, 170, 180, 131, 90
See application file for complete search history.

(56) References Cited

U.S. PATENT DOCUMENTS

| 6,099,465 A | 8/2000 | Inoue |
| 8,385,043 B2 | 2/2013 | Ng et al. |

(Continued)

FOREIGN PATENT DOCUMENTS

| CN | 107785151 A | 3/2018 |
| EP | 0632654 A1 | 1/1995 |

OTHER PUBLICATIONS

Extended European Search Report Application No. 19000077.8 Completed Date: Mar. 17, 2019; dated Mar. 27, 2019 5 Pages.
(Continued)

*Primary Examiner* — Elvin G Enad
*Assistant Examiner* — Kazi S Hossain
(74) *Attorney, Agent, or Firm* — Whitmyer IP Group LLC

(57) ABSTRACT

A transformer includes a substrate having an input and an output, the input being connectable to one section of a medical electrical device, the output being connectable to another section of the medical electrical device. An input ground system and an output ground system, which is electrically isolated from the input ground system, provide continuous return paths for an input signal and an output signal, respectively. The transformer includes a primary winding electrically connected to the input, a secondary winding electrically connected to the output, and a core transferring data from the primary winding to the secondary winding using magnetic field coupling. A middle portion of the primary winding and a middle portion of the secondary winding wrap around the core and are twisted together. Other portions of the primary winding are twisted with one another, while other portions of the secondary winding are twisted with one another.

24 Claims, 10 Drawing Sheets

(51) Int. Cl.
*H01F 27/24* (2006.01)
*H01F 27/28* (2006.01)
*H02J 50/80* (2016.01)
*H01F 27/06* (2006.01)
*H01F 27/26* (2006.01)
*H01F 19/04* (2006.01)
*H01F 27/02* (2006.01)
*A61B 1/00* (2006.01)
*A61N 1/08* (2006.01)
*H01F 19/08* (2006.01)

(56) References Cited

U.S. PATENT DOCUMENTS

| | | | |
|---|---|---|---|
| 2005/0088267 A1* | 4/2005 | Watts | G05F 7/00 |
| | | | 336/178 |
| 2012/0176756 A1* | 7/2012 | Gailus | H01R 13/6633 |
| | | | 361/752 |
| 2015/0304139 A1* | 10/2015 | Mo | H03H 7/00 |
| | | | 375/257 |
| 2017/0033762 A1 | 2/2017 | O'Toole | |
| 2018/0062678 A1* | 3/2018 | Ragonese | H01F 19/04 |

OTHER PUBLICATIONS

European Search Report Application No. 18000764.3 Completed: Jan. 7, 2019; dated Jan. 15, 2019 7 Pages.
GenesisRadio G40 40m Xcvr Builders' Notes. Feb. 16, 2018. http://www.wb5rvz.com/sdr/genesis_g40/g40/10_pa.htm, pp. 1-9, (downloaded: Feb. 20, 2018).

* cited by examiner

HIGH SPEED DATA TRANSFORMER FOR PATIENT ISOLATION BARRIER

TECHNICAL FIELD

The present disclosure generally relates to the field of communications transformers used in, for example, medical electrical equipment and medical electrical systems. More specifically, the present disclosure relates to a transformer apparatus for protecting equipment and individuals from electric shock while providing high speed, high frequency data transfer across an isolation barrier.

BACKGROUND

For medical equipment and systems, there exist strict requirements for basic safety, essential performance, and electromagnetic compatibility. International Electrotechnical Commission 60601 (herein "IEC 60601"; equivalent to EN 60601) is a series of standards which establishes a benchmark for medical electrical equipment, wherein compliance to these standards is a prerequisite for commercializing medical equipment in many countries. Under IEC 60601-1, medical electrical equipment is defined as any electrical equipment which has an applied part or transfers energy to or from a patient or detects such energy transfers to or from the patient and which is provided with not more than one connection to a particular supply mains and is intended to be used in diagnosis, treatment, or monitoring of a patient.

One example of a medical electrical device or system is an endoscopic video system. Endoscopic video systems are now used with an endoscope(s) in general surgery. The endoscope, for example, may be a passive optical device, on which a camera head may be releasably attached. The camera head contains electronic circuitry including a charge coupled device (CCD) or complementary metal oxide semiconductor (CMOS) image sensor. An umbilical connects the camera head to a video processing support unit that obtains operating power from commercial power mains, and provides a ground-reference video output. Safety regulations, such as IEC 60601-1, require that electrical isolation be provided between the camera head(s) which makes physical contact with the patient and the processing electronics.

While communications transformers by themselves are not medical devices, and are therefore, not directly covered by the IEC 60601-1 standards, they are nevertheless integral to the design and operation of medical equipment and medical systems (e.g., endoscopic video systems). A communications transformer provides DC (direct current) electrical isolation of one circuit from another, impedance transformation, common-mode signal suppression, and a safety insulation barrier to meet safety requirements. The transformer should also exhibit low insertion loss and high return loss in order to maximize transmitted power and minimize channel echo effects across a transmit signal's bandwidth.

For prior art transformers, the requirements of electrical isolation and safety insulation barrier are difficult to meet when trying to achieve high speed or high frequency data transfer rates. Some prior art transformers are able to satisfy the isolation barrier requirements set forth in IEC 60601-1, but are not designed to provide a high data rate bandwidth, for example for transmitting high resolution video data (e.g., 4K resolution video/images). This drawback results in limiting the use of such transformers to low or medium data-rate applications, or alternatively, adversely limiting the transmission speed of an electrical equipment or system which incorporates the prior art transformer. With the advancement and development of communication technology, an increasing number of medical applications may require signal bandwidths of 1200 MHz or more. However, these prior art transformers are inadequate for such high frequencies applications.

Other conventional transformers may be designed for higher data transfer rates. Such transformers are often used in RF applications and transmit electromagnetic energy by way of the transverse electromagnetic mode, instead of by the coupling of magnetic flux. However, these conventional transformers fail to meet the isolation barrier requirements set forth in IEC 60601-1 and possess poor low-frequency common-mode rejection. The conventional transformers do not provide high-voltage electrical isolation, and as such, are unacceptable for use in medical equipment or systems, as they may pose a shock hazard.

Thus, there exists a need in the art for an improved transformer which has the capacity to provide high frequency data transfer while providing (or exceeding) sufficient electrical isolation necessary for medical electrical equipment and medical electrical systems, such as that which is specified by safety standards (e.g., EN/IEC 60601-1).

SUMMARY

The needs set forth herein as well as further and other needs and advantages are addressed by the present teachings, which illustrate solutions and advantages described below.

It is an object of the present teachings to remedy the above drawbacks and issues associated with prior art transformers.

It is another object of the present teachings to provide a transformer that is configured for a defined bandwidth or a range of bandwidths and further has sufficient galvanic isolation between two sections of a medical electrical device or system, as defined by IEC 60601-1 (EN 60601-1) standards.

It is an object of the present teachings to provide a transformer that transfers high frequency data across an isolation barrier, which electrically isolates two sections of a medical electrical device or system, in accordance with IEC 60601-1 (EN 60601-1) standards.

It is a further object of the present teachings to create a transformer that provides ground isolation between isolated and non-isolated sections of a device motherboard.

It is still another object of the present teachings to provide a transformer which exhibits an insertion loss below a prescribed limit and a return loss above a prescribed limit to meet or exceed essential performance characteristics required by IEC 60601-1 (EN 60601-1) for medical electrical equipment or medical electrical systems.

It is a further object of the present teachings to provide a transformer which has the capacity for high frequency data transfer and galvanic isolation between two sections of an electrical device, and which prevents or attenuates unwanted field noise, electrostatic discharge (ESD), electrical fast transients (EFT), surges transients, and/or cross-talk passing through the isolation barrier. The transformer should minimize any loss in data integrity.

It is an additional object of the present teachings to provide a transformer which meets or exceeds the requirements established for medical electrical equipment and medical electrical systems by IEC 60601-1 (EN 60601-1) standards.

These and other objects of the present teachings are achieved by providing a transformer or transformer apparatus comprising a substrate having an input side and an output side, the input side being connectable to one section of a medical electrical device, the output side being connectable to another section of the medical electrical device. The substrate has an input ground system and an output ground system which is electrically isolated from the input ground system. The input ground system and the output ground system provide independent continuous return paths for an input signal and an output signal, respectively. The transformer further includes a magnetic core mounted to the substrate, as well as a primary winding and a secondary winding. The primary winding has a first primary end and a second primary end connected to a positive pad and a negative pad of the input side, wherein the primary winding has a middle portion that wraps around the core, an anterior portion between the first primary end and the middle portion, and a posterior portion between the second primary end and the middle portion. The secondary winding has a first secondary end and a second secondary end connected to a positive pad and a negative pad of the output side, wherein the secondary winding has a middle portion that wraps around the core, an anterior portion between the first secondary end and the middle portion, and a posterior portion between the second secondary end and the middle portion. The core is configured to transfer data from the primary winding to the secondary winding using magnetic field coupling. The middle portion of the primary winding and the middle portion of the secondary winding are twisted together. Further, the anterior portion and the posterior portion of the primary winding are twisted together, while the anterior portion and the posterior portion of the secondary winding are twisted together.

The present teachings also provide a transformer or transformer apparatus comprising a substrate which is composed of a plurality of layers stacked on top of each other. The layers include a top layer, a bottom layer, and multiple intervening layers disposed between the top layer and the bottom layer. All of the layers provide a multi-moat electrical isolation between an input side and an output side. The substrate has an input ground system and an output ground system which is electrically isolated from the input ground system, wherein the input ground system and the output ground system provide continuous return paths for an input signal and an output signal, respectively. The input side of the substrate has a positive pad and a negative pad in the top layer, as well as a positive connection terminal and negative connection terminal in the bottom layer. The positive pad and the negative pad are electrically connected to the positive connection terminal and the negative connection terminal, respectively, by vertical interconnect access components. Similarly, the output side of the substrate has a positive pad and a negative pad in the top layer, as well as a positive connection terminal and a negative connection terminal in the bottom layer, wherein the positive pad and the negative pad of the output side are electrically connected to the positive connection terminal and the negative connection terminal of the output side, respectively, by vertical interconnect access components. The connection terminals of the input side are connectable to one section of a medical electrical device and the connection terminals of the output side are connectable to another section of the medical electrical device. The transformer also includes a magnetic core mounted on the top layer of the substrate, wherein the core helps to electrically isolate the two sections of the medical electrical device. The core itself is also electrically isolated from the two sections. A primary winding has a first primary end and a second primary end connected to the positive pad and a negative pad of the input side. The primary winding has a middle portion that wraps around the core, an anterior portion between the first primary end and the middle portion, and a posterior portion between the second primary end and the middle portion. A secondary winding has a first secondary end and a second secondary end connected to the positive pad and the negative pad of the output side. The secondary winding has a middle portion that wraps around the core, an anterior portion between the first secondary end and the middle portion, and a posterior portion between the second secondary end and the middle portion. The core is configured to transfer data from the primary winding to the secondary winding using magnetic field coupling. In addition, the middle portion of the primary winding and the middle portion of the secondary winding are twisted together. The arrangement of the substrate, core, primary winding, and secondary winding provides an isolation barrier between the two sections of the medical electrical device.

With the above configuration, the transformer or transformer apparatus according to the present teachings provides electrical isolation between two sections of a medical device that meets or exceeds EN/IEC 60601-1 requirements for a patient isolation barrier. For example, the transformer is able to maintain between 4000 V and 4500 V AC electrical isolation for at least one minute duration between two sections of a device. It also can provide 5000 V DC electrical isolation for at least 2.5 ms duration between two sections of a device. The transformer allows for bandwidth control techniques while passing high speed data over the isolation barrier. Another advantageous aspect of the transformer is that it attenuates or prevents unwanted pulses from being passed over the isolation barrier. Further, the transformer provides impedance control techniques at the input and output sides of the transformer while passing the isolation barrier, which isolates and separates the returns paths for the input side and the output side.

Other exemplary electrical specifications and properties that the transformer provides, offers, and/or achieves include an operating bandwidth of 300 MHz to 3000 MHz and a capacity to exclude or attenuate unwanted noise within the bandwidth range. The insertion loss of the transformer within the operating frequencies, for example, is 9.0 dB. The return loss of the transformer is for example 4.0 dB within the operating frequencies. The transformer according to the present teachings can transfer data from approximately 100 Mbps to 6 Gbps.

Other features and aspects of the invention will become apparent from the following detailed description, taken in conjunction with the accompanying drawings, which illustrate by way of example the features in accordance with embodiments of the invention. The summary is not intended to limit the scope of the invention, which is defined solely by the claims attached thereto.

BRIEF DESCRIPTION OF THE DRAWINGS

It should be understood that through the drawings, corresponding reference numerals indicate like or corresponding parts and features.

DETAILED DESCRIPTION

The present teachings are described more fully hereinafter with reference to the accompanying drawings, in which the present embodiments are shown. The following description illustrates the present teachings by way of example, not by way of limitation of the principles of the present teachings.

The present teachings have been described in language more or less specific as to structural features. It is to be understood, however, that the present teachings are not limited to the specific features shown and described, since the devices herein disclosed comprise preferred forms of putting the present teachings into effect.

Figure 1:
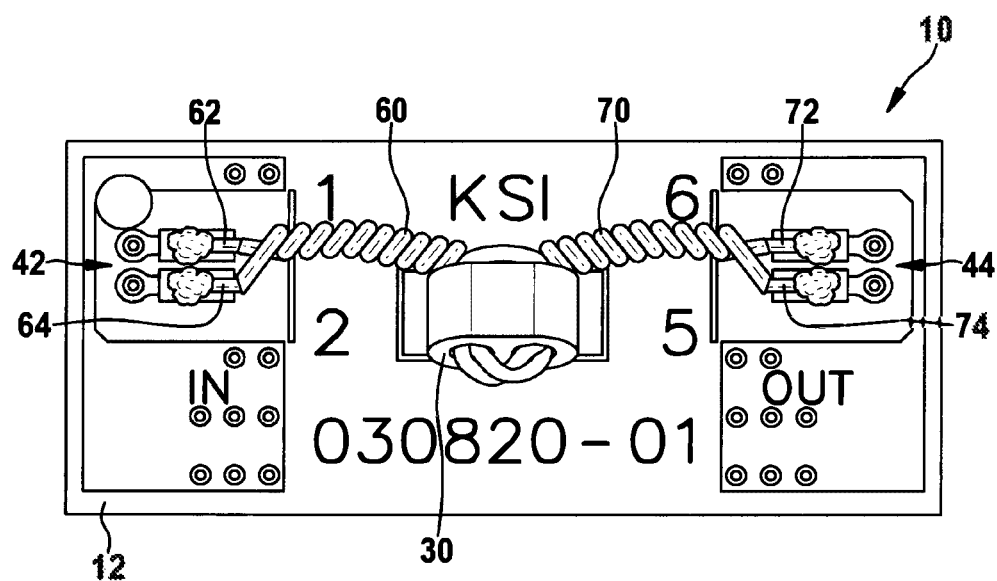
FIG. 1 is a top view of a transformer or transformer apparatus in accordance with the present teachings, wherein the transformer or transformer apparatus can be integrated or implemented in a medical equipment or medial system.
Figure 2:
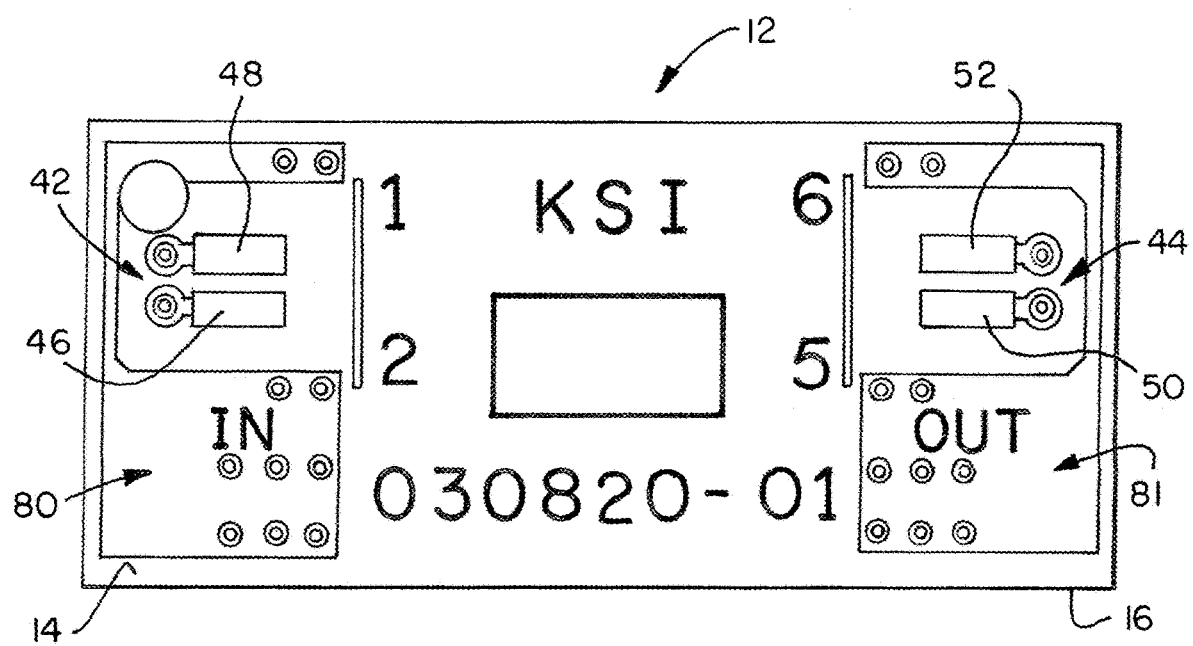
FIG. 2 is a top view of a substrate forming the transformer or transformer apparatus of FIG. 1.

FIG. 1 shows a top view of the transformer or transformer apparatus 10 according to the present teachings. The transformer 10 comprises a substantially planar substrate 12, having an upper surface 14 and an opposing lower surface 16, as illustrated in FIG. 2. The substrate 12 is formed by a plurality of layers oriented substantially parallel to one another. In some embodiments, the substrate is a circuit board or the like. Although the substrate is described herein as a circuit board, it will be understood by those with skill in the art that any type of wafer substrate is also within the scope of the present teachings. The transformer 10 further includes a core 30 and windings 60, 70 partially surrounded by the core. The arrangement of the substrate, core, and the windings as shown in FIG. 1 creates a transformer configured to transfer high frequency data within an exemplary bandwidth range of 300 MHz to 3.00 GHz, while providing electrical isolation and insulation barrier characteristics necessary for medical equipment and medical systems.

Figure 3:
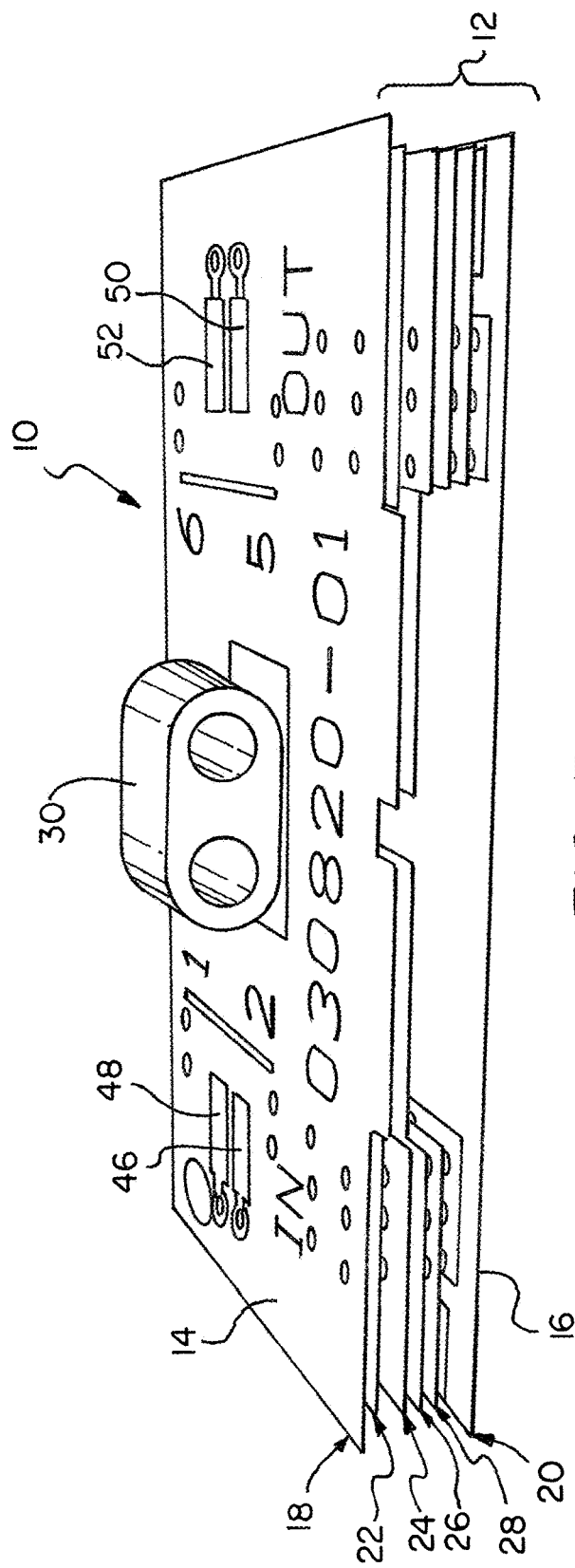
FIG. 3 is a partially exploded view of the transformer or transformer apparatus of FIG. 1, wherein the substrate comprises multiple layers and the core is mounted on the top layer of the substrate.

FIGS. 2-3 show the substrate 12 of FIG. 1 in more detail. The substrate has a design structure which provides signal integrity for the entire specified bandwidth of the transformer and further provides sufficient electrical isolation to exceed patient isolation barrier requirements of safety standards (e.g., EN/IEC 60601-1). The substrate 12 comprises a plurality of layers fixed to each other in a substantially parallel relationship with one another. Each layer has upper and lower planar surfaces, wherein the planar surfaces of adjacent layers are substantially flush with one another. A top layer 18 has an upper planar surface which constitutes the upper surface 14 of the substrate 12. The lower surface 16 of the substrate is formed by the lower planar surface of a bottom layer 20. Intervening layers disposed between the top layer 18 and the bottom layer 20 are configured as ground layers providing sufficient electrical isolation to exceed IEC 60601-1 standards, while maintaining ground continuity and separate return paths for an input side and an output side of the transformer. FIG. 3, in particular, shows that the substrate 12 includes four intervening layers 22, 24, 26, 28. Although this embodiment is described with respect to the substrate 12 having four intervening layers, those of skill in the art will understand that a substrate including any number of intervening layers is within the scope of the present teachings. For example, more than four intervening layers may be present between the top layer and the bottom layer. Yet, in other embodiments, there may be as few as two or three intervening layers. With the configuration of the intervening layers, the substrate achieves the required electrical isolation barrier and ground continuity essential for medical equipment and medical systems. The layers 18-28 of the substrate may comprise an insulating material having a low coefficient of thermal expansion for example. This allows the substrate to withstand hot-spot temperatures of, for example, 180° C. The insulating material may have a dielectric strength between 1000 and 2000 V per mil (1 mil=1/1000 inch) and a low dielectric constant (e.g., 4.0-5.0). The insulating material therefore minimizes capacitance between the layers, and in turn, reduces the parasitic capacitance of any magnetic components implemented in the substrate layers.

Figure 4A:
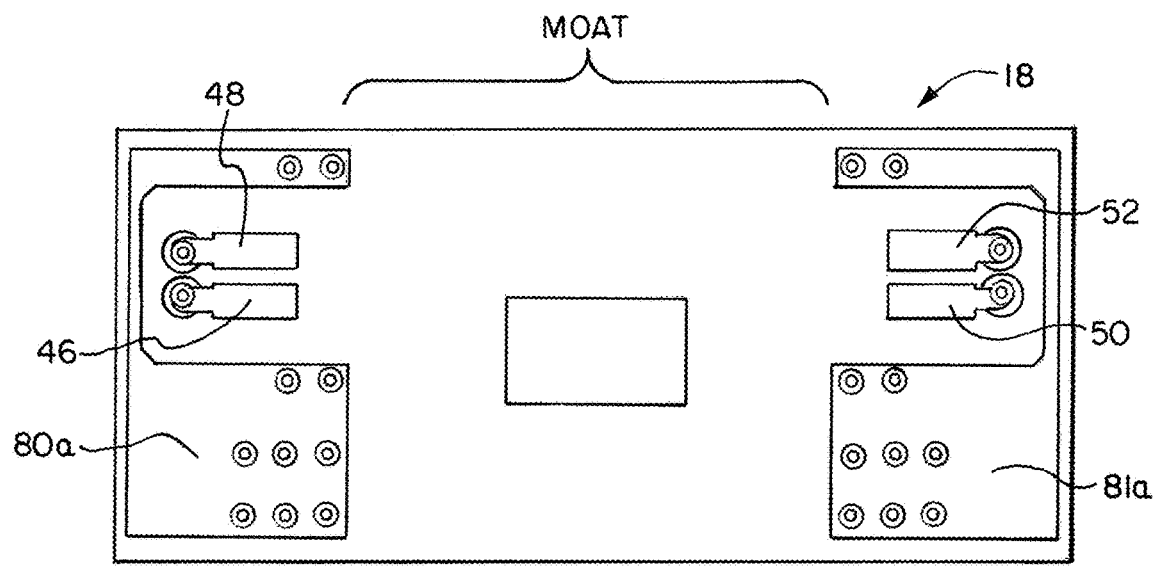
FIGS. 4a-4f are plan views of various layers making up the substrate of the transformer or transformer apparatus of FIG. 1.
Figure 4B:
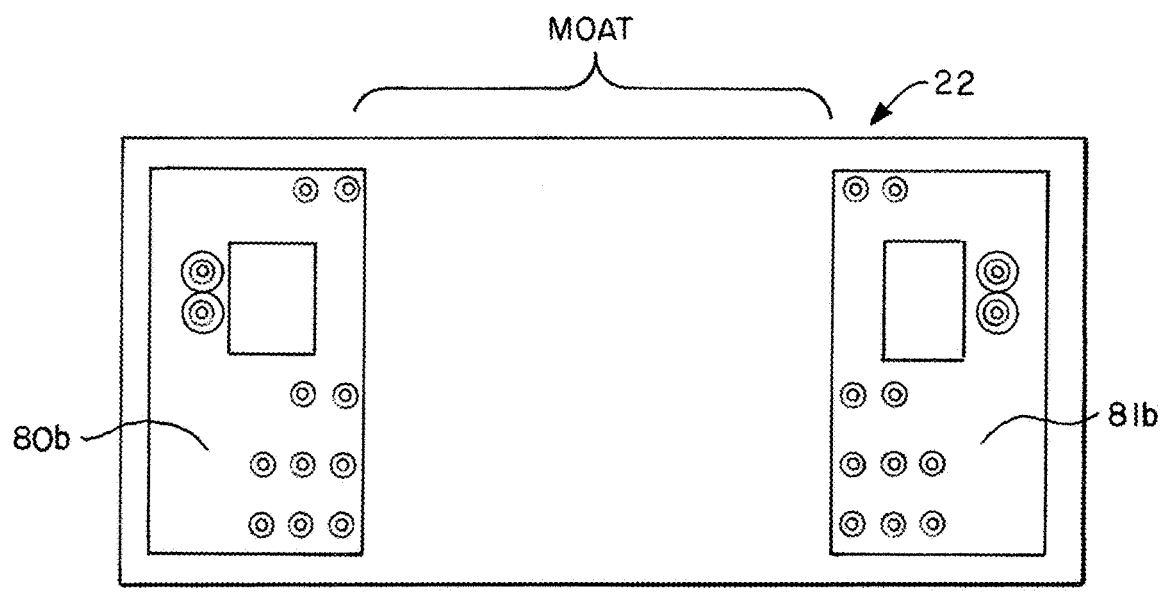
Figure 4C:
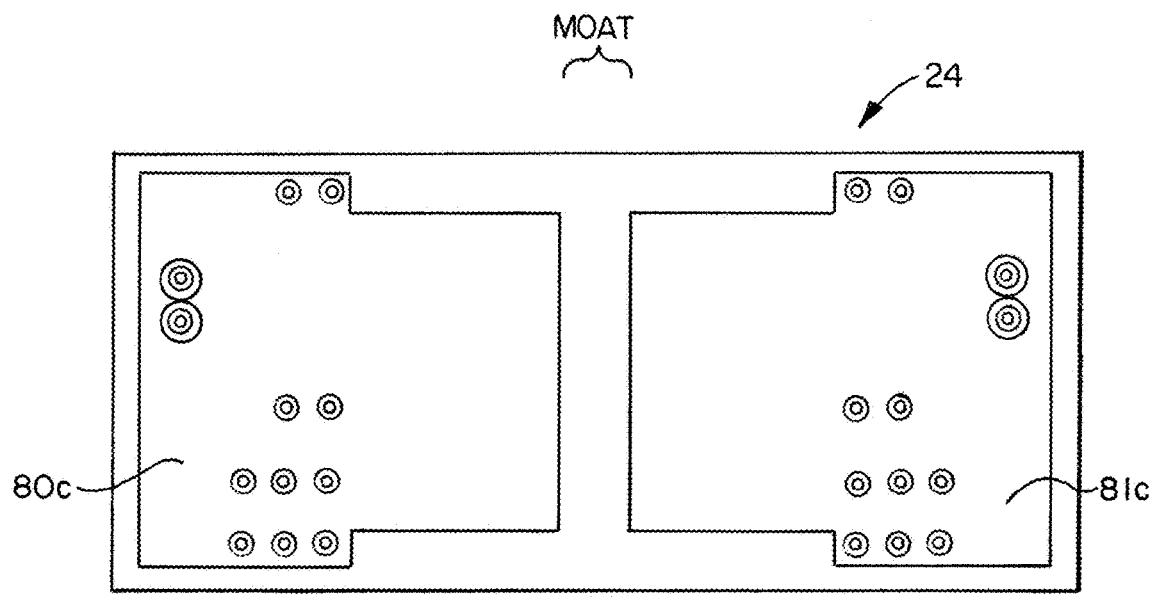
Figure 4D:
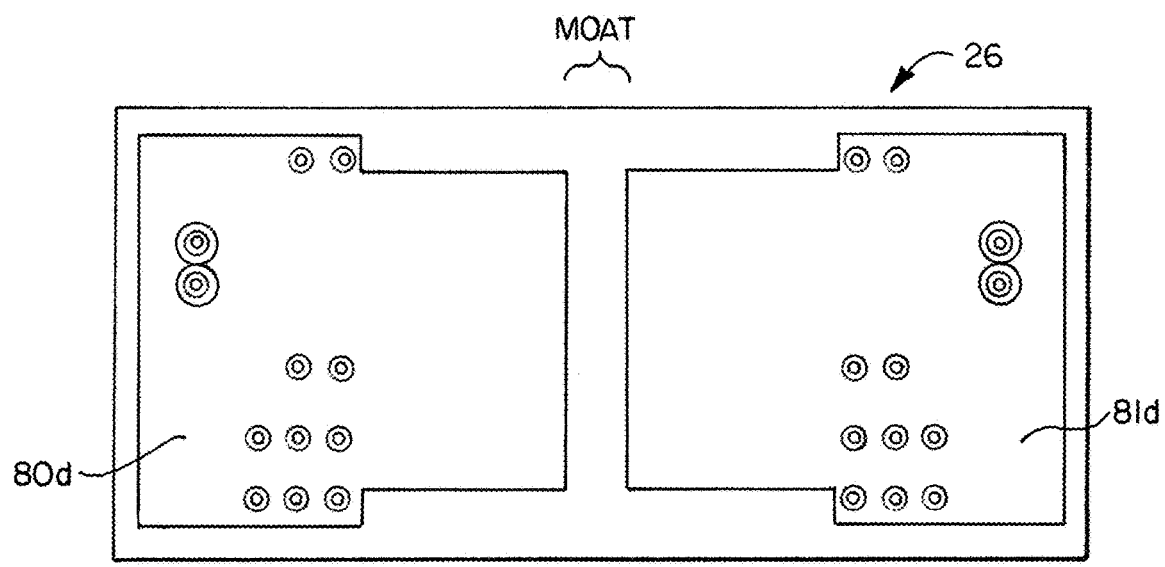
Figure 4E:
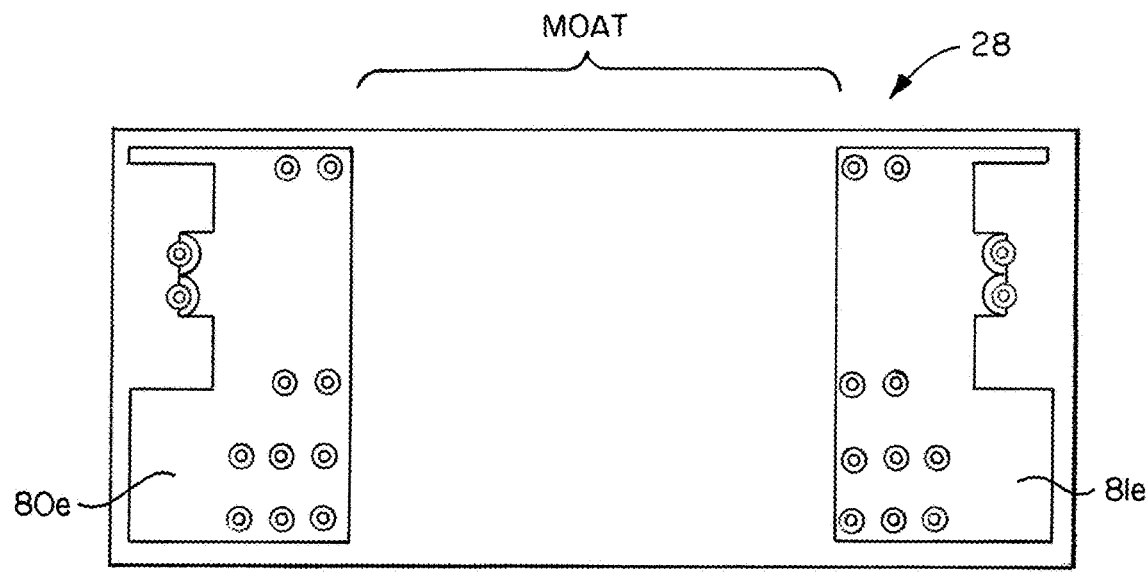
Figure 4F:
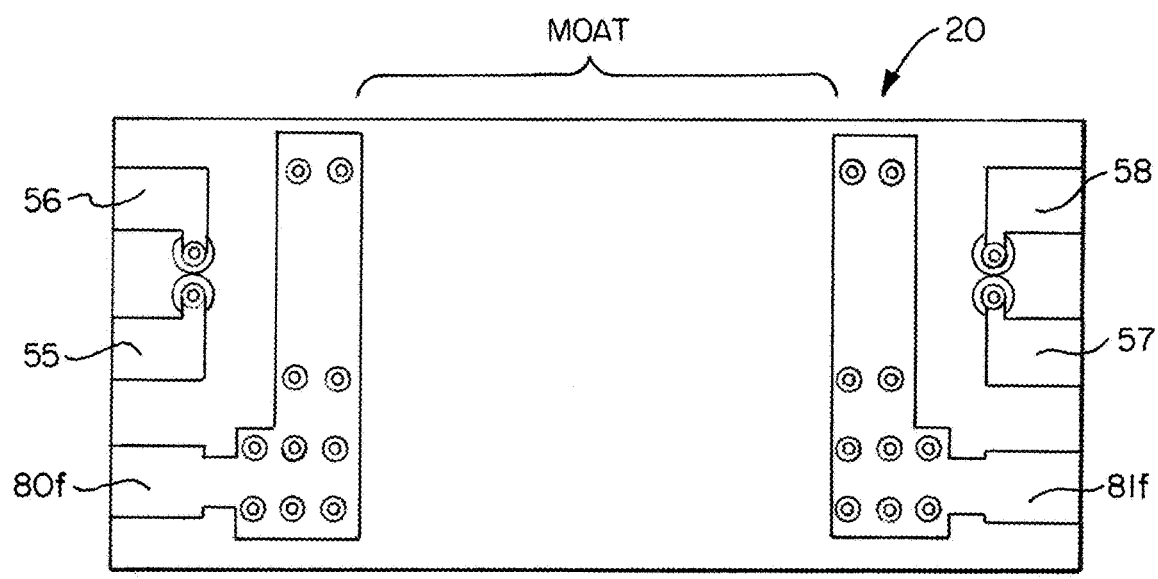

The substrate 12 has a dual ground system for the input side and the output side of the transformer 10. As shown in FIG. 2, a ground network 80 is configured for the input side of the transformer, while the output side of the transformer has a ground network 81. The ground network 80 is formed by multiple ground planes in each of the layers of the substrate. In particular, the ground network 80 comprises a ground plane 80a in the top layer 18 (FIG. 4a), a ground plane 80b in the second layer 22 (FIG. 4b), a ground plane 80c in the third layer 24 (FIG. 4c), a ground plane 80d in the fourth layer 26 (FIG. 4d), a ground plane 80e in the fifth layer 28 (FIG. 4e), and a ground plane 80f in the bottom layer 20 (FIG. 4f). In similar respect, the ground network 81 for the output side of the transformer comprises ground planes in each of the substrate layers, including a ground plane 81a in the top layer 18 (FIG. 4a), a ground plane 81b in the second layer 22 (FIG. 4b), a ground plane 81c in the third layer 24 (FIG. 4c), a ground plane 81d in the fourth layer 26 (FIG. 4d), a ground plane 81e in the fifth layer 28 (FIG. 4e), and a ground plane 81f in the bottom layer 20 (FIG. 4f). This dual ground system provided in the substrate 12 gives the input side/section and output side/section of the transformer their own continuous return paths from the upper surface 14 to the lower surface 16 of the substrate. The shapes and dimensions of the ground planes in each layer are designed so that creepage and clearance requirements for patient isolation barrier (EN/IEC 60601-1) are satisfied. For example, the ground planes 80a and 81a on the top layer 18 have general shapes resembling a letter C and a backwards C. The ground plane 80a thus surrounds partially the conductive pads 46, 48. As shown in FIG. 4a, the ground plane 80a does not extend on the right side of the conductive pads, where stripped ends of the primary winding 60 are soldered to the pads (FIG. 1). The same configuration applies to the ground plane 81a, which does not extend on the left side of the conductive pads 50, 52, where stripped ends of the secondary winding 70 are soldered to the pads. Contrasting the ground planes 80a and 81a, the ground planes 80b-f and 81b-f include ground paths that are arranged in areas of the respective substrate layer which are vertically aligned with the positions where the windings are soldered to the respective conductive pads. Each ground plane in layers 20-28 has a specific size and shape to meet the requirements for creepage, clearance and isolation barrier (EN/IEC 60601-1). FIGS. 4a-4f demonstrate that the ground network 80, formed by ground planes 80a-80f, establish a return path continuation for input signals with no interruption. Similarly, the ground network 81, formed by ground planes 81a-81f, establish a return path continuation for output signals with no interruption. The provision of independent continuous return paths for input signals and for output signals is a key feature of the present teachings.

Another main feature of the dual ground system of the substrate 12 is that the ground networks 80 and 81 are electrically isolated from each other. The substrate has two sections (i.e., input side, output side) that are isolated from one another by a dynamic multi moat technique, thereby meeting isolation barrier requirements. By making the ground networks isolated from one another, the ground network 80 can be configured to function and correspond with an isolated section of a medical device, while the ground network 81 is configured to function and correspond with a non-isolated section of the device, or vice versa. Electrical isolation between the ground networks is achieved through separation using multi moat technology. In the top layer 18, the ground planes 80a and 81a are arranged on opposing ends of the substrate 12 and are separated from each other by a copper-free moat, i.e., middle region of the top layer having non-conductive material (FIG. 4a). The intervening layers 22-28 and bottom layer 20 also have moats to maintain electrical isolation of the ground networks 80 and 81 throughout the substrate. The ground networks 80 and 81 therefore provide two isolated return paths for two isolated signals (e.g., input and output). The ground network 80 preserves input signal integrity in combination with the primary winding 60, as well as preserves input signal integrity in combination with the conductive pads 46, 48 on the input side. Similarly, the ground network 81 preserves output signal integrity in combination with the secondary winding 70 and preserves output signal integrity in combination with conductive pads 50, 52 on the output side.

The substrate 12, as shown in FIGS. 2-3 and 4a, includes two impedance control sections that are electrically isolated from one another. An input section or side 42 is arranged on the top layer 18 of the substrate 12 and is constructed with a positive conductive pad 48 and a negative conductive pad 46. The pads 48, 46 are configured to be connected (e.g., soldered) to the ends of the primary winding 60. On the opposing side of the substrate, an output section or side 44 is provided on the top layer 18. A positive conductive pad 52 and a negative conductive pad 50 of the output side 44 are connected (e.g., soldered) to the ends of the secondary winding 70. The primary and secondary windings will be described in more detail below. The input and output sides 42, 44 of the substrate are designed such that they satisfy creepage and clearance requirements for patient isolation barrier (EN/IEC 60601-1).

Figure 5:
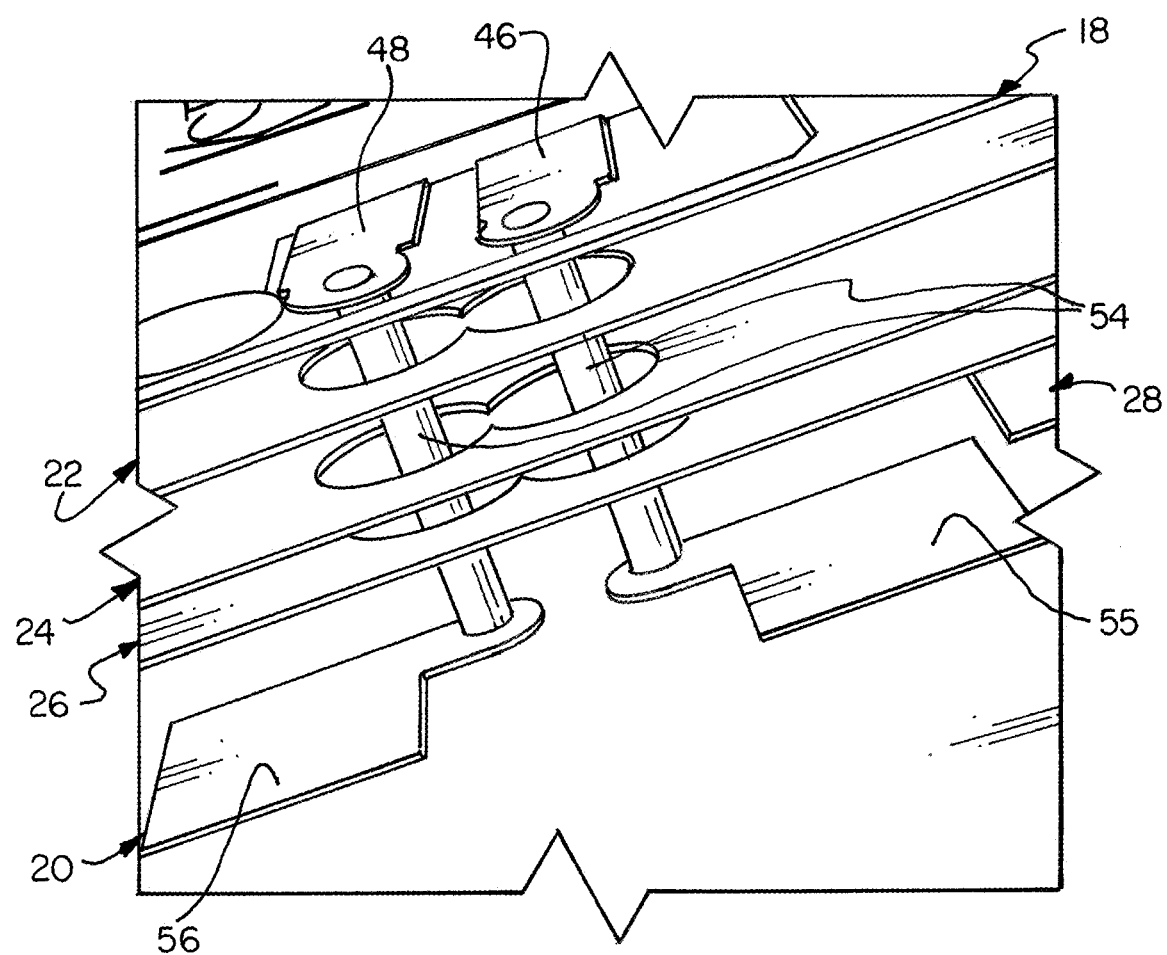
FIG. 5 is an exploded view of the substrate forming the transformer or transformer apparatus of FIG. 1.

In FIG. 5, each conductive pad 46-52 has a vertical interconnect access 54 extending from the top layer 18 to the bottom layer 20 through the intervening layers 22, 24, 26, 28. Although FIG. 5 shows only one side of the substrate 12, specifically the side having pads 46, 48 of the input side 42, the pads 50, 52 of the output side 44 have the same configuration with respect to the vertical interconnect access 54 extending from the top layer 18 to the bottom layer 20. Each vertical interconnect access 54 has one end electrically connected to the respective conductive pad and an opposing end electrically connected to a terminal 55, 56, 57, 58 disposed in the bottom layer 20 (FIG. 4f). Specifically, a first vertical interconnect access electrically connects the positive pad 48 to a positive input terminal 56, while a second vertical interconnect access electrically connects the negative pad 46 to a negative input terminal 55. A third vertical interconnect access electrically connects the positive pad 52 to a positive output terminal 58, while a fourth vertical interconnect access electrically connects the negative pad 50 to a negative output terminal 57. In preferred embodiments, the vertical interconnects 54 extend orthogonally relative to the layers of the substrate. In other embodiments, different forms of electrical connection other than the vertical interconnect access may be used to electrically connect the conductive pads on the top layer 18 of the substrate to the input/output terminals on the bottom layer 20. The input/output terminals 55-58 are configured to respectively connect to a motherboard of the medical device, or to one or more other substrates (e.g., printed circuit boards). Whereas the conductive pads 46, 48, 50 and 52 provide impedance controlled connections to the twisted wire pairs of the primary winding 60 and the secondary winding 70, the input/output terminals 55-58 provide impedance controlled connections to the motherboard of the medical device.

Referring back to FIG. 2, the ground networks 80 and 81, the input side 42, and the output side 44 are shown in an exemplary arrangement. The location, size and shape of these substrate components help to meet and/or exceed the creepage and clearance requirements under EN/IEC 60601-1. The box illustrated in the center of the upper substrate surface 14 defines an area in which the core 30 is mounted to the substrate. The distance between the area for core mounting and the conductive pads 46-52 is enough to satisfy creepage and clearance requirements. The distance between the area for core mounting and the pads 50, 52 of the output section 44 (or the pads 46, 48 of the input section 42) is, for example, approximately 3.5 mm. FIG. 2 also depicts two demarcation lines along the input side and the output side. The demarcation lines define the limit in which the stripped ends of the primary winding 60 and the stripped ends of the secondary winding 70 may extend. For example, the primary winding 60 is stripped—i.e., insulation sleeve is removed—at its ends (which are connected to the pads 46, 48 of the input side 42) towards the core 30, but no further than the left demarcation line. The secondary winding 70 is stripped at its ends towards the core 30, but not past the right demarcation line. The limits for the position of stripped wires support the transformer in meeting or exceeding creepage and clearance requirements.

As shown in FIG. 1, the transformer 10 is formed with the primary winding 60 and the secondary winding 70. Each winding comprises a conductor, such as a copper wire. However, other types of conductors may be used as the windings, and are within the scope of the present teachings. The primary winding and the secondary winding are characterized as having sufficient insulation to meet safety standards for medical electrical equipment, such as insulated winding wire minimum test requirements within EN/IEC 60601-1. For example, the windings may comprise a fluoropolymer insulation. The insulation of each winding has at least 1500 Vrms dielectric withstand strength. Both primary winding 60 and secondary winding 70 include twisted pairs (discussed in further detail below) which can provide 4500 V to 5000 V AC electrical isolation for one-minute duration. The windings are also adapted to provide 5000 V DC electrical isolation for 2.5 ms duration. For both primary winding 60 and the secondary winding 70, when the winding is twisted, 100 ohm differential impedance is created. More specifically, the sections of the primary winding 60 that are twisted together maintain 100 ohm differential impedance by adjusting the twist density or rate, i.e., number of twists per unit length. The sections of the secondary winding 70 that are twisted together also maintain 100 ohm differential impedance by adjusting the twist density. In contrast, the respective sections of the primary winding 60 and the secondary winding 70 that are not twisted together maintain 100 ohm differential impedance by adjusting the substrate with respect to the configuration of the ground networks 80 and 81. The primary and secondary windings are adapted to transfer the high frequency portion of the defined bandwidth of the transformer using electrical coupling data transfer means.

The transformer 10 also includes the magnetic core 30 (FIGS. 1 and 3). The core 30 is typically formed of a ferrous material. The core 30 is installed and mounted on the top layer 18 of the substrate 12 using, for example, an electrically non-conductive adhesive. Thus, there is no possibility for conduction of electricity between the substrate and the core. The core 30 is adapted to transfer low frequency data from the input wire (e.g., primary winding) to the output wire (e.g., secondary winding). That is, the core can transfer data at the required low frequency portion (e.g., 300-500 MHz) of the defined bandwidth of the transformer, using magnetic field data transfer technology. In some embodiments, the core 30 has a limited bandwidth that can start at lower frequencies (e.g., 100 MHz), while in other embodiments, the core has a limited bandwidth that can start at higher frequencies. Moreover, the core is configured such that it does not transfer lower frequency signals of unwanted field noise, electrostatic discharge (ESD), electrical fast transients (EFT), and surges transients that are outside of the defined bandwidth range of the transformer to the secondary winding.

Figure 6:
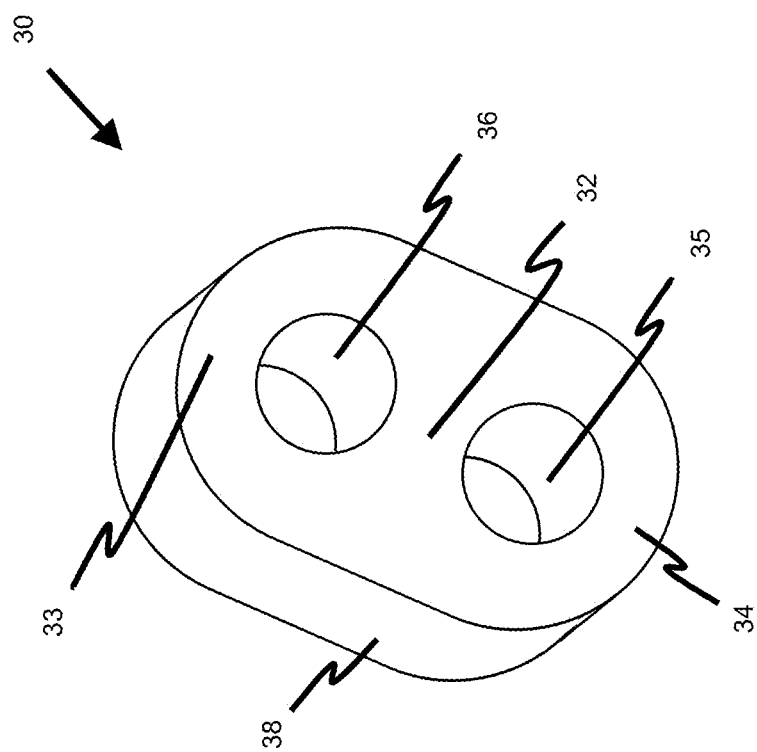
FIG. 6 is a perspective view of a core forming the transformer or transformer apparatus of FIG. 1.

In FIG. 6, the core 30 is shown prior to the primary winding 60 and the secondary winding 70 being wound thereon. In some embodiments, the core 30 has a binocular or shell type construction, wherein the primary winding 60 and the secondary winding 70 pass inside the core (magnetic circuit) which forms a shell around the windings. The core has three limbs or legs, including a central leg 32 and two side legs 33, 34 spaced apart from the central leg by two openings or channels 35, 36. The windings are looped around the central leg 32 one or more times, and a flux path is completed through the two side legs 33, 34. The central leg 32 carries the total mutual flux, while the side legs forming a part of a parallel magnetic circuit carry half the total flux. Alternate core constructions (e.g., core-type) may be used for the core 30 in order to provide the required low frequency portion of the defined bandwidth of the transformer. Additionally, in some embodiments, at least one layer of parylene coating 38 is applied on the core, including within the channels 35 and 36. The coating helps in providing better isolation between the windings and the core for the life of the transformer. In other embodiments, two or more layers of parylene coating 38 are applied to the core. However, it is noted that the windings 60, 70 are configured with sufficient insulation such that the core 30 may not need any parylene coating. In other embodiments, different insulating materials (organic or inorganic) may be used to coat the core, such as a silicone-based insulator.

Figure 7:
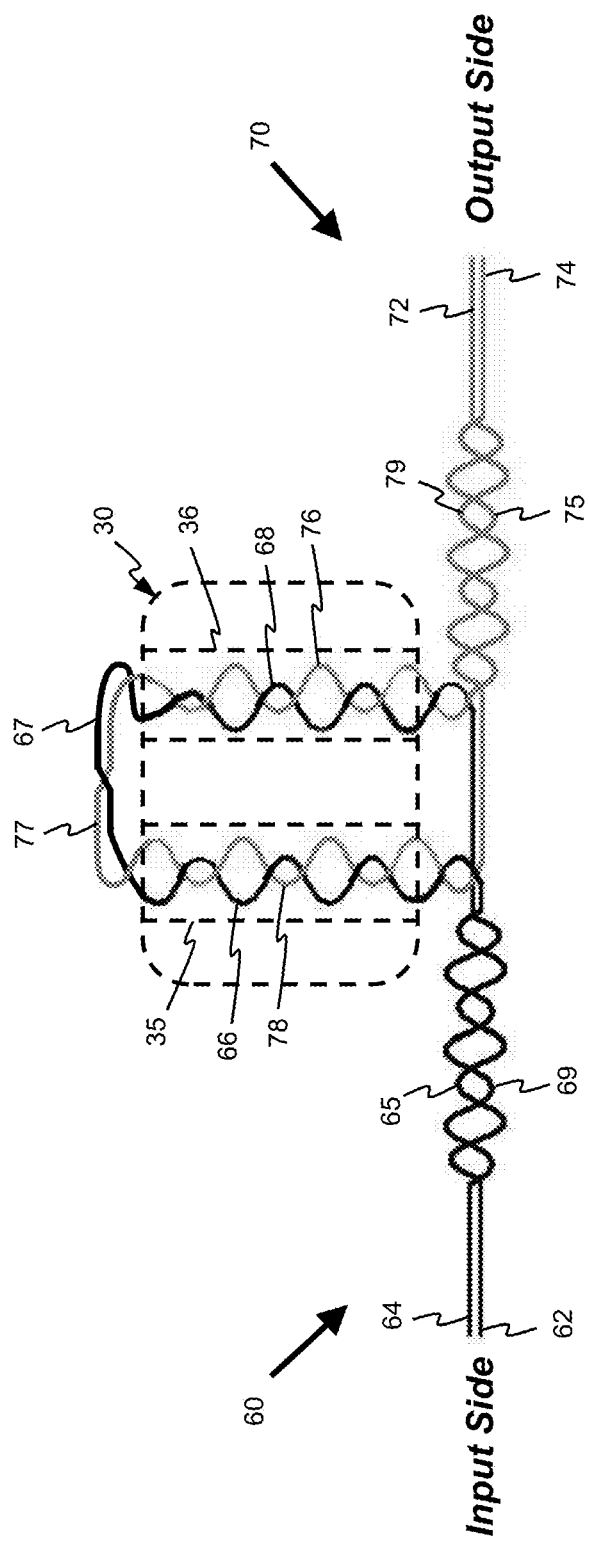
FIG. 7 is a schematic view of the wire arrangement of primary and secondary windings of the transformer or transformer apparatus of FIG. 1.

In some embodiments, the primary winding 60 and secondary winding 70 are each configured with only one turn around the core 30. That is, both windings loop around the central leg 32 only one time (FIGS. 1 and 7). However, in other embodiments, both the primary and secondary windings loop multiple times around the central leg 32, i.e., the windings have more than one turn around the core. The primary winding and the secondary winding may also be configured to have the same number of turn(s) or alternatively, different number of turn(s). A first end 62 of the primary winding 60 is connected (e.g., soldered) to the positive pad 48 of the input side 42, while a second, opposite end 64 is connected (e.g., soldered) to the negative pad 46 of the input side 42. A first end 72 of the secondary winding 70 is connected (e.g., soldered) to the positive pad 52 of the output side 44. The second, opposite end 74 is connected (e.g., soldered) to the negative pad 50 of the output side 44.

In order to achieve a high frequency data transfer, the primary winding and the secondary winding have a particular wire configuration (e.g., twisting arrangement). FIG. 7 shows the transformer with a one-loop winding configuration, as well as the twisting of the primary winding and the twisting of the secondary winding. It is noted that the embodiment of FIG. 7 is exemplary, and the present teachings are not limited thereto. The number of twisted primary and secondary windings can be less than one wind or more than one wind. The number of primary winding across the core can also be different than the number of secondary winding across the core. As shown in FIG. 7, the primary winding 60 can be identified by five sections 65, 66, 67, 68, and 69. Sections 65 and 66 designate segments of the primary winding between the first end 62 and a middle section 67, which is located at or approximately in the middle between the first end 62 and the second end 64. Sections 68 and 69 designate segments of the primary winding 60 between the middle section 67 and the second end 64. In similar respect, the secondary winding 70 is divided into five sections 75, 76, 77, 78, and 79. Sections 75 and 76 designate segments of the secondary winding 70 between the first end 72 and a middle section 77, which is located at or approximately in the middle between the first end 72 and the second end 74. Sections 78 and 79 designate segments of the secondary winding 70 between the middle section 77 and the second end 74.

The first end 62 of the primary winding 60 is connected to the positive conductive pad 48 of the input side 42, while the second end 64 of the primary winding 60 is connected to the negative conductive pad 46 of the input side 42. In preferred embodiments, the connections of the first end 62 and second end 64 to the positive and negative pads 48, 46 are created by soldering. As shown in FIG. 1, the ends 62, 64 of the primary winding 60 are stripped and are not covered by an insulating sleeve. The first end 72 and the second end 74 of the secondary winding 70 are also stripped and are soldered to the positive conductive pad 52 and the negative conductive pad 50 of the output side 44. Referring back to FIG. 7, the primary winding 60 (at sections 66, 67, and 68) is looped around the central leg 32 of the core 30 one time. Similarly, the secondary winding 70 (at sections 76, 77, and 78) is looped around the central leg 32 of the core 30 one time. Other embodiments of the transformer, however, may be configured such that the primary winding 60 is looped around the central leg 32 multiple times (e.g., 2, 3, 4, etc. loops) and/or the secondary winding 70 is looped around the central leg 32 multiple times. It is further noted that the number of primary winding loops across the core can be different than the number of secondary winding loops across the core.

The primary winding 60 and secondary winding 70 each incorporate a specific twisting arrangement depending on the particular section of the respective wire. Sections 65 and 69 of the primary winding 60, which are adjacent to the first and second ends 62, 64, are twisted together such that they resemble a twisted pair. Likewise, sections 75 and 79 of the secondary winding 70, which are adjacent to the ends 72, 74, are twisted together. However, for the remaining portions of the primary winding and the secondary winding, the two windings are twisted with one another. Specifically, section 66 of the primary winding 60 is disposed within one of the channels (i.e., channel 35) of the core, while section 67 extends between channel 35 and channel 36, thereby wrapping around one side of the central leg 32. Section 68 of the primary winding 60 is disposed within the other core channel (i.e., channel 36). The secondary winding 70 has section 76 disposed within the channel 36 and section 78 disposed within the channel 35. As shown in FIGS. 1 and 7, section 77 of the secondary winding is positioned on the same side of the core as section 67 of the primary winding. Section 66 of the primary winding is twisted with section 78 of the secondary winding. Further, sections 67 and 77 are twisted together, and sections 68 and 76 are twisted together. The portion of the primary winding between sections 68 and 69—which is disposed outside the channels of the core 30—is also twisted with the portion of the secondary winding between sections 78 and 79. However, for ease of illustration, FIG. 7 does not show this particular twisting of the primary winding and the secondary winding. Nevertheless, in some embodiments, the portion of the primary winding between sections 68 and 69 may not be twisted with the portion of the secondary winding between sections 78 and 79. Additionally, other embodiments may have no twisting between section 67 of the primary winding and section 77 of the secondary winding. The above unique twisting of the primary winding and the secondary winding helps to provide data transfer at high frequencies (e.g., greater than 500 MHz) and at high data rates (e.g., 100 Mbps to 6 Gbps).

The number of twists and the number of twists per length (e.g., inch) in each of the sections 65-69 of the primary winding and the section 75-79 of the secondary winding can vary depending on the communications specifications required by a medical equipment or system. The length of the section that the primary winding and the secondary winding are twisted will affect the transfer gain and phase at a high frequency portion of the bandwidth. The twisted wire impedance, as well as the wire soldering to the conductive pads (on the top layer 18 of the substrate), may affect the data transfer rate and noise at higher bandwidths. As an example, as shown in FIG. 1, sections 65 and 69 of the primary winding 60 are twisted together at least three times. Likewise, sections 75 and 79 of the secondary winding 70 include at least three twists. Also within each channel of the core, the primary and secondary windings may be twisted so that one or more twists are present. With respect to sections 67 and 77, the primary winding and the secondary winding are arranged with half of a twist in FIG. 1. However, in other embodiments, the sections 67 and 77 may include one complete twist or more than one twist.

The primary and secondary windings are magnetically coupled to one another by way of their magnetic fluxes through the transformer core when the primary winding and the secondary winding conduct current. As a result, the combination of the primary winding, the second winding, the core and the substrate on which the core is mounted form the transformer or transformer apparatus.

Figure 8:
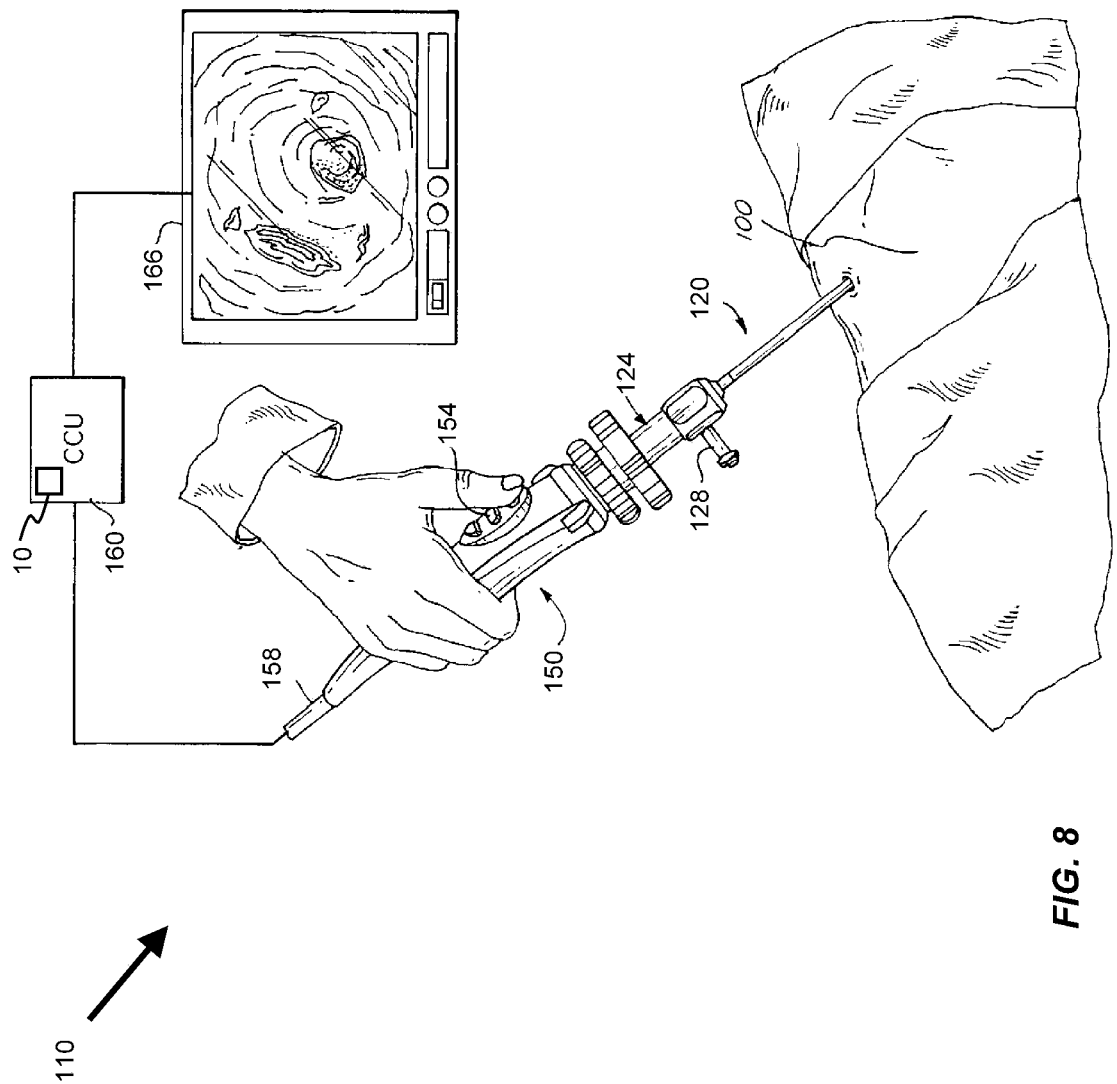
FIG. 8 is a schematic view of the transformer or transformer apparatus of FIG. 1 integrated or implemented in a medical equipment or system.

FIG. 8 shows as an example of the transformer or transformer apparatus 10 incorporated, implemented, or integrated into the camera control unit 160 of an endoscopic system 110. The transformer is used to provide high frequency data transfer while maintaining electrical isolation between two sections of the endoscopic system 110. As shown in FIG. 8, the endoscopic system 110 comprises an endoscope 124, which has a shaft 120 partially inserted into a patient 100. The endoscope may comprise a light port 128 for connecting a light source. The endoscope 124 may be connected to a detachable camera head 150 having user control buttons 154, wherein communication between the endoscope and the camera head is performed optically. A cable or umbilical cord 158 connects the camera head 150 to the camera control unit 160, providing communication between these system components. Further, the camera control unit 160 can be communicatively connected to a monitor 166 or another computer over a network, such as the Internet.

When the transformer or transformer apparatus is installed, integrated, or implemented into a device, such as the camera control unit 160 of the endoscopic system 110, the input side/section or the output side/section of the transformer may be the isolated side of the CCU's motherboard, while the output side/section or the input side/section may be the non-isolated portion of the CCU's motherboard. This means that the transformer design of the present teachings can be used in both directions and provide data transfer in both directions.

The combination of the substrate, core, primary winding, and secondary winding according to the present teachings creates a transformer or transformer apparatus that provides electrical isolation which exceeds the safety standards established under EN/IEC 60601-1. The substrate according to the present teachings electrically isolates the primary winding from the secondary winding. The insulation coating (e.g., parylene coating) of the core increases electrical isolation of the transformer. Moreover, the wires of the primary winding and the secondary winding have insulation which adds to the isolation characteristics of the transformer. Thus, the electrical insulation of the substrate, the core coating, and the windings cooperate to meet or exceed the required electrical isolation for medical equipment or systems, as specified in EN/IEC 60601-1. In addition to providing patient isolation barrier, the transformer or transformer apparatus provides creepage protection (e.g., sufficient creepage distance) and clearance between an isolated section of a device/system (e.g. medical device, medical system, etc.) and a non-isolated section of the medical device/system.

The transformer or transformer apparatus in accordance with the present teachings further provides high data rate communication between an isolated section of a device/system and a non-isolated section of the device/system (e.g., medical device, medical system, etc.). The high data rate is achieved by way of the following factors: substrate provides controlled impedance and signal integrity for data transfer through the substrate and through soldered portions of the primary and secondary windings; electrical data transfer through the twisted pair; and magnetic data coupling between the core and the windings. High frequency data at either the isolated section of a device motherboard, or the non-isolated section of the motherboard, would be transferred from the motherboard to the transformer input. The high frequency data would be transferred through microstrip routing using the substrate multi-level ground system and coplanar routing which controls and maintains signal integrity to pass high frequency data, while also filtering very high frequency unwanted noise.

The above implementation of the transformer or transformer apparatus is compact and thus can be implemented or integrated into the circuitry of any type of medical equipment or system, especially for medical equipment where there has been an emphasis on minimization (e.g., endoscopes). Moreover, the transformer as described herein can handle relatively large amounts of heat, and has a low parasitic capacitance and leakage inductance. Furthermore, the transformer is configured to handle high data rates, as is needed for high resolution video, such as HD (high definition), UHD (ultra-high definition), and 4K resolution video, and transfer more data across a patient isolation barrier. As high definition technology advances, physicians and medical companies expect medical systems to incorporate new technology and deliver high quality video with 4K resolution. This higher resolution, in turn, requires much higher data rates.

It should be understood to a person of ordinary skill in the art that different configurations of the transformer apparatus are possible. For example, the design layout of the transformer apparatus may differ from those shown in the Figures without departing from the scope and spirit of the present teachings.

While the present teachings have been described above in terms of specific embodiments, it is to be understood that they are not limited to those disclosed embodiments. Many modifications and other embodiments will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

What is claimed is:

1. A transformer comprising:
   a substrate having an input side and an output side, the input side being connectable to one section of a medical electrical device, the output side being connectable to another section of the medical electrical device, the substrate having an input ground system and an output ground system which is electrically isolated from the input ground system, the input ground system and the output ground system providing independent continuous return paths for an input signal and an output signal, respectively;
   a magnetic core mounted to the substrate;
   a primary winding having a first primary end and a second primary end connected to a positive pad and a negative pad of the input side, the primary winding having a middle portion that wraps around the core, an anterior portion between the first primary end and the middle portion, and a posterior portion between the second primary end and the middle portion;
   a secondary winding having a first secondary end and a second secondary end connected to a positive pad and a negative pad of the output side, the secondary winding having a middle portion that wraps around the core, an anterior portion between the first secondary end and the middle portion, and a posterior portion between the second secondary end and the middle portion;
   the core transferring data from the primary winding to the secondary winding using magnetic field coupling;
   wherein the middle portion of the primary winding and the middle portion of the secondary winding are twisted together; and
   wherein the anterior portion and the posterior portion of the same primary winding are twisted together, while the anterior portion and the posterior portion of the same secondary winding are twisted together.

2. The transformer of claim 1, wherein the primary winding and the secondary winding are configured to transfer a high frequency portion of a transformer bandwidth using electrical coupling data transfer.

3. The transformer of claim 1, wherein the core is configured to transfer a low portion of a transformer bandwidth using magnetic field coupling data transfer.

4. The transformer of claim 1, wherein the core comprises a center limb and two side limbs positioned on opposite sides of the center limb, the middle portions of the primary winding and the secondary winding being wrapped around the center limb through gaps between the center limb and the side limbs.

5. The transformer of claim 4, wherein the primary winding and the secondary winding each wrap around the center limb of the core one time.

6. The transformer of claim 4, wherein the primary winding wraps around the core multiple times and the secondary winding wraps around the center limb of the core multiple times.

7. The transformer of claim 1, wherein the primary winding and the secondary winding each comprises a conductor with insulation, the conductor being configured to provide 5000 V DC electrical isolation for at least 2.5 ms duration.

8. The transformer of claim 7, wherein each of the twisted pair of the anterior and posterior portions of the primary winding and the twisted pair of the anterior and posterior portions of the secondary winding provide 4500 V AC electrical isolation for at least 1 minute duration.

9. The transformer of claim 8, wherein the twisting of the primary and secondary windings provides a 100 ohm differential impedance.

10. The transformer of claim 9, wherein the portions of the primary and secondary windings that are twisted maintain substantially the 100 ohm differential impedance by adjusting twist density, while portions of the primary and secondary windings that are not twisted maintain substantially 100 ohm differential impedance by adjusting the input ground system and the output ground system.

11. The transformer of claim 7, wherein the conductor with insulation is rated for 1500 Vrms dielectric withstand strength.

12. The transformer of claim 7, wherein the first primary end and second primary end of the primary winding are stripped of the insulation, the first primary end and the second primary end being soldered to the positive pad and the negative pad of the input side;
   wherein the first secondary end and the second secondary end of the secondary winding are stripped of the insulation, the first secondary end and the second secondary end being soldered to the positive pad and the negative pad of the output side; and
   wherein the pads of the input side and the pads of the output side provide impedance controlled connections to the twisted primary winding and the twisted secondary winding, respectively.

13. The transformer of claim 1, wherein the substrate comprises a top layer forming a top surface of the substrate, a bottom layer forming a bottom surface of the substrate, and a plurality of intervening layers disposed between the bottom layer and the top layer, and
   wherein each of said top layer, bottom layer, and intervening layers has two separate ground planes to form a part of the input ground system and a part of the output ground system, said layers incorporating multiple moats separating the ground planes of the input ground system from the ground planes of the output ground system to electrically isolate the continuous return path of the input from the continuous return path of the output.

14. The transformer of claim 13, wherein the positive pad and the negative pad of the input side and the positive pad and the negative pad of the output side are disposed on the top layer of the substrate;
   wherein the bottom layer of the substrate comprises two input connection terminals associated with the input side and two output connection terminals associated with the output side;
   wherein the substrate comprises vertical interconnect access components, a first vertical interconnect access component connects the positive pad of the input side to one of the input connection terminals, a second vertical interconnect access component connects the negative pad of the input side to the other of the input connection terminals, a third vertical interconnect access component connects the positive pad of the output side to one of the output connection terminals, and a fourth vertical interconnect access component connects the negative pad of the output side to the other of the output connection terminals; and
   wherein said input and output connection terminals provide impedance controlled connections to two different sections of a motherboard of the medical electrical device.

15. The transformer of claim 13, wherein the multiple moats of the layers are positioned substantially along a vertical axis which is perpendicular to a plane of the substrate, the core being mounted on a top surface of the substrate in a position corresponding with the vertical axis.

16. The transformer of claim 1, wherein the core has at least two coatings of parylene.

17. The transformer of claim 1, wherein the core, primary winding, and the secondary winding are configured to transfer data at a rate between 100 Mbps and 6 Gbps.

18. The transformer of claim 1, wherein the substrate, core, primary winding, and second winding provide an isolation barrier between the sections of the medical electrical device, which meet or exceed IEC 60601-1 requirements.

19. A transformer comprising:
   a substrate having a plurality of layers stacked on top of each other, said layers including a top layer, a bottom layer, and multiple intervening layers disposed between the top layer and the bottom layer, all of the layers providing a multi-moat electrical isolation between an input side and an output side of the substrate, the substrate having an input ground system and an output ground system which is electrically isolated from the input ground system, the input ground system and the output ground system providing continuous return paths for an input signal and an output signal, respectively;
   the input side having a positive pad and a negative pad in the top layer and a positive connection terminal and a negative connection terminal in the bottom layer, the positive pad and the negative pad being electrically connected to the positive connection terminal and the negative connection terminal, respectively by vertical interconnect access components;
   the output side having a positive pad and a negative pad in the top layer and a positive connection terminal and a negative connection terminal in the bottom layer, the positive pad and the negative pad of the output side being electrically connected to the positive connection terminal and the negative connection terminal of the output side, respectively by vertical interconnect access components;
   the connection terminals of the input side being connectable to one section of a medical electrical device and the connection terminals of the output side being connectable to another section of the medical electrical device;
   a magnetic core mounted on the top layer of the substrate;
   a primary winding having a first primary end and a second primary end connected to the positive pad and the negative pad of the input side, the primary winding having a middle portion that wraps around the core, an anterior portion between the first primary end and the middle portion, and a posterior portion between the second primary end and the middle portion;
   a secondary winding having a first secondary end and a second secondary end connected to the positive pad and the negative pad of the output side, the secondary winding having a middle portion that wraps around the core, an anterior portion between the first secondary end and the middle portion, and a posterior portion between the second secondary end and the middle portion;
   the core transferring data from the primary winding to the secondary winding using magnetic field coupling;
   wherein the middle portion of the primary winding and the middle portion of the secondary winding are twisted together; and
   wherein the substrate, core, primary winding, and secondary winding provide an isolation barrier between the sections of the medical electrical device.

20. The transformer of claim 19, wherein the anterior portion and the posterior portion of the same primary winding are twisted together, while the anterior portion and the posterior portion of the same secondary winding are twisted together.

21. The transformer of claim 19, wherein the input side and output side are located on opposing sides of the substrate, the core being positioned between the input side and the output side.

22. The transformer of claim 19, wherein the core is a binocular-type core.

23. The transformer of claim 19, wherein the primary winding and the secondary winding are configured to transfer a high frequency portion of a transformer bandwidth using electrical coupling data transfer and the core is configured to transfer a low portion of a transformer bandwidth using magnetic field coupling data transfer.

24. The transformer of claim 1, wherein the core, primary winding, and the secondary winding are configured to transfer data at a rate between 100 Mbps and 6 Gbps.

* * * * *